United States Patent

Kakimoto et al.

[11] Patent Number: 5,266,704
[45] Date of Patent: Nov. 30, 1993

[54] PROCESS FOR PRODUCTION OF 2-SUBSTITUTED-4-HYDROMETHYLIMIDAZOLE COMPOUNDS

[75] Inventors: Takehiko Kakimoto, Gifu; Toshima Ogawa, Ogaki, both of Japan

[73] Assignee: Nippon Gohsei Kagaku Kogyo Kabushiki Kaisha, Osaka, Japan

[21] Appl. No.: 940,380

[22] Filed: Sep. 3, 1992

[30] Foreign Application Priority Data

Sep. 6, 1991 [JP] Japan .................. 3-255848

[51] Int. Cl.$^5$ .................. C07D 233/60; C07D 233/54
[52] U.S. Cl. .................. 548/341.1
[58] Field of Search .................. 548/341.1

[56] References Cited

U.S. PATENT DOCUMENTS

| 4,074,054 | 2/1978 | Christidis et al. | 548/341.1 |
| 4,107,308 | 8/1978 | Paul et al. | 548/341.1 X |
| 4,567,276 | 1/1986 | Baldwin | 544/3 |
| 4,719,309 | 1/1988 | Mesch et al. | 548/341.1 |
| 4,851,526 | 7/1989 | Greenberg et al. | 544/370 |
| 4,853,383 | 8/1989 | Baldwin et al. | 544/139 |

OTHER PUBLICATIONS

Hofmann, K., *Imidazole and its Derivatives*, Part I, New York, pp. 33-38 (1953).

Primary Examiner—Floyd D. Higel
Attorney, Agent, or Firm—Armstrong, Westerman, Hattori, McLeland & Naughton

[57] ABSTRACT

The invention provides a process for producing a 2-substituted-4-hydroxymethylimidazole easily and in good yield by means of simple equipment. This process comprises reacting hydroxymethylglyoxal, a monoaldehyde and ammonia in a sequence such that said monoaldehyde and ammonia are first reacted with each other and hydroxymethylglyoxal is then introduced into the reaction system for further reaction.

8 Claims, No Drawings

PROCESS FOR PRODUCTION OF 2-SUBSTITUTED-4-HYDROMETHYLIMIDAZOLE COMPOUNDS

FIELD OF THE INVENTION

The present invention relates to a process for producing a 2-substituted-4-hydroxymethylimidazole which is a useful synthetic intermediate for the manufacture of drugs.

BACKGROUND OF THE INVENTION

As a production technology for a 2-alkyl-4-hydroxymethylimidazole compound, the U.S. Pat. No. 4107308 describes a process comprising reacting butyronitrile with gaseous hydrogen chloride in a lower alkanol solvent to prepare an iminoether compound, reacting this intermediate compound with gaseous ammonia to give butyramidine hydrochloride and further reacting this butyramidine hydrochloride with liquid ammonia in the presence of 1,3-dihydroxyacetone dimer, which process is claimed to give the desired compound in a yield of 58%. However, because it involves the use of hydrogen chloride gas and ammonia gas, this method requires special equipment and entails various problems such as corrosion and pollution, thus being disadvantageous for commercial purposes.

Under the circumstances the inventors of the present invention explored in earnest to develop a method for producing the object compound in good yield using simple equipment and found that the above objective can be realized by reacting a monoaldehyde with ammonia in the first place and, then, introducing hydroxymethylglyoxal into the system for further reaction. The present invention has been developed on the basis of the above finding.

SUMMARY AND DESCRIPTION OF THE INVENTION

The present invention is characterized by the above-mentioned reactants and reaction sequence and any other reaction schema, such as charging the starting materials in one step or en bloc, cannot achieve the object.

The monoaldehyde can be an aliphatic aldehyde such as acetaldehyde, propionaldehyde, valeraldehyde, n-butyraldehyde, etc. or an aromatic aldehyde such as benzaldehyde, and each of them yields the corresponding 2-substituted-4-hydroxymethylimidazole.

For this reaction, the preferred molar ratio of hydroxymethylglyoxal, monoaldehyde and ammonia is 1.0/1.0–2.0/2.0–3.0. This reaction is conducted in an aqueous medium, but an organic solvent may be used in a small proportion in combination with water.

In conducting the reaction, the monoaldehyde and ammonia are first introduced into the aqueous medium for reaction. Typically, ammonia is first introduced (aqueous ammonia) and, then, the monoaldehyde is added dropwise or en bloc.

The monoaldehyde can be used as it is but in order to improve its solubility in aqueous medium, it is more advantageous to use a solution of the monoaldehyde in an organic solvent such as methanol or ethanol.

The reaction temperature may be about 10° to 60° C. and is preferably about 20° to 40° C. The reaction time is preferably in the range of about 1.0 to 5.0 hours. Thereafter, hydroxymethylglyoxal is introduced into the system and the reaction is further continued. While this reactant can be added en bloc, it is preferably added dropwise.

The reaction temperature in this stage may be about 10° to 60° C. and is preferably 20° to 40° C. The reaction time may practically range from about 1.0 to 5.0 hours. After completion of charging, the reaction system is maintained for about 0.5 to 2.0 hours to complete the reaction. The object compound is then isolated from the reaction mixture by the per se known procedure such as extraction. Where necessary, the object compound is purified by the known method such as treatment with activated carbon.

It is thus, apparent that the process of this invention is very advantageous from commercial points of view in that 2-substituted-4-hydroxymethylimidazole compounds of value as intermediates for the manufacture of drugs can be produced easily and in good yield by means of simple equipment.

The following examples are further illustrative of the present invention.

EXAMPLE 1

A reaction vessel was charged with 47.2 g (0.694 mole) of 25% aqueous ammonia and 47.2 g of water and the mixture was stirred with ice-cooling. Then, a solution prepared by dissolving 27.1 g (0.315 mole) of valeraldehyde in 100 g of methanol was added over a period of 15 minutes. Thereafter, with the internal temperature of the reaction vessel being maintained at 30° C., 137.89 g of a 20% aqueous solution of hydroxymethylglyoxal [20.67 g (0.235 mole) on a solids basis] was added dropwise over a period of 1.5 hours. After completion of dropwise addition, the reaction mixture was maintained at the same temperature for 30 minutes.

The resulting reaction mixture was concentrated in a rotary evaporator to recover 112.19 g of a residue (27.17 g of 2-butyl-4-hydroxymethylimidazole). To the residue was added 141.13 g of water and, then, 18.38 g of 35% hydrochloric acid was added over a period of 30 minutes to give 2-butyl-4-hydroxymethylimidazole hydrochloride. This solution was extracted at 50° C. The bottom layer was separated, treated with activated carbon and filtered. To the filtrate was added 28.2 g of 25% sodium hydroxide solution, whereupon crystals of 2-butyl-4-hydroxymethylimidazole separated out. The crystals were recovered by filtration, rinsed and dried to give 25 g of 2-butyl-4-hydroxymethylglyoxal. The yield based on hydroxymethylglyoxal was 70% (purity 95%).

EXAMPLE 2

The procedure of Example 1 was repeated except that 100 g (1.47 moles) of 25% aqueous ammonia, 42.63 g (0.735 mole) of 100% propionaldehyde and 215.6 g (0.735 mole) of 40% hydroxymethylglyoxal were used. The yield of the resulting 2-propyl-4-hydroxymethylimidazole was 70% (purity 96%).

CONTROL EXAMPLE

A reaction vessel was charged with 100 g (1.47 moles) of 25% aqueous ammonia, 215.6 g (0.735 mole) of 40% hydroxymethylglyoxal, 63.3 g (0.735 mole) of valeraldehyde and 233.6 g of methanol, all en bloc, and the reaction was continued for 2 hours.

Gas chromatographic analysis of the resulting reaction mixture showed that the yield of 2-butyl-4-hydroxymethylimidazole was as low as 10%.

What is claimed is:

1. A process for producing a 2-substituted-4-hydroxymethylimidazole by reacting hydroxymethylglyoxal, a monoaldehyde and ammonia, consisting of first reacting said monoaldehyde and ammonia with each other and then introducing said hydroxymethylglyoxal into the reaction system for further reaction.

2. The process of claim 1 wherein hydroxymethylglyoxal is added dropwise.

3. The process of claim 1 wherein said monoaldehyde is an aliphatic aldehyde or an aromatic aldehyde.

4. The process of claim 3 wherein said aliphatic aldehyde is propionaldehyde.

5. The process of claim 3 wherein said aliphatic aldehyde is valeraldehyde.

6. The process of claim 3 wherein said aromatic aldehyde is benzaldehyde.

7. The process of claim 1 wherein the reaction is conducted in aqueous medium..

8. The process of claim 1 wherein the reaction is conducted in a mixture of water and an organic solvent.

* * * * *